United States Patent [19]

Timpl et al.

[11] Patent Number: 4,798,800
[45] Date of Patent: Jan. 17, 1989

[54] PROCESS FOR ISOLATING HUMAN GLOBULAR DOMAIN NC1 OF BASAL MEMBRANE COLLAGEN FROM HUMAN TISSUE

[75] Inventors: Rupert Timpl, Gauting; Dietrich Brocks, Hünfelden, both of Fed. Rep. of Germany

[73] Assignee: Max-Planck-Gesellschaft Zur Foederung Der Wissenschaften e.V., Göttingen, Fed. Rep. of Germany

[21] Appl. No.: 664,538

[22] Filed: Oct. 25, 1984

[30] Foreign Application Priority Data

Mar. 19, 1984 [DE] Fed. Rep. of Germany ....... 3410049

[51] Int. Cl.$^4$ ............................ C07K 3/02; C07K 3/22; C07K 15/20
[52] U.S. Cl. ....................................... 435/273; 435/69; 530/356; 530/416; 530/848; 530/835; 530/849
[58] Field of Search ............... 530/356, 353, 416, 417; 435/268, 273, 265, 267, 272, 169

[56] References Cited

U.S. PATENT DOCUMENTS 4,340,581 7/1982 Timpl .................................. 530/356

OTHER PUBLICATIONS

Timpl et al, "A Network Model for Organization of Type IV Collagen Molecules in Basement Membranes" European Journal of Biochemistry 120 pp. 203–211 (1981).
Weber et al, "Subunit Structure and Assembly of the Globular Domain of Basement Membrane Collagen Type IV", *Eur J Biochem*, vol. 139:401–410 (1984)(Mar. 1st).
Risteli et al, "7-S Collagen: Characterization of an Unusual Basement Membrane Structure", *Eur. J. Biochem*, vol. 108:239–250(1980).

*Primary Examiner*—John Tarcza
*Attorney, Agent, or Firm*—Felfe & Lynch

[57] ABSTRACT

The present invention provides human characterized by a molecular weight of about 170,000 Dalton, a hexameric structure with monomeric subunits with a molecular weight of about 28,000 Dalton and a carbohydrate content of about 2%.

The present invention provides a process for obtaining and purifying globular domain NC1 of basal membrane collagen, wherein human or animal tissue is subjected to a first limiting treatment with bacterial collagenase, the degradation products obtained are separated from non-collagen proteins by chromatography on a weakly basic anion exchanger, the collagen degradation products are then subjected to a second collagenase digestion at an elevated temperature and the globular domain NC1 is purified by molecular sieve fractionation.

Furthermore, the present invention is concerned with the use of this for the determination in body fluids in the case of the use of their antibodies, as well as far the detection of antibodies directed thereagainst in body fluids.

7 Claims, No Drawings

PROCESS FOR ISOLATING HUMAN GLOBULAR DOMAIN NC1 OF BASAL MEMBRANE COLLAGEN FROM HUMAN TISSUE

The present invention is concerned with the human globular domain NC1 of basal membrane collagen (Type IV), with a simple process for the isolation of the domain NC1 from various human and animal tissues and with the use of the said human protein fragment for the immunological determination of basal membrane components in body fluids and of auto-immune reactions against basal membranes.

In the case of a large number of diseases some of which occur frequently, such as diabetes, vasculities, nephropaties, neurofibroma, liver fibrosis and epithelial tumours, a change of the basal membranes result, such as thickening or disintegration, especially in the walls of the vessels. These changes often represent lethal complications. The detection of such changes can take place by means of electron microscopy or immunofluorescence but require biopsy material and only permit qualitative statements. Recently, it could be shown on appropriate animal models, for example streptozocin diabetes in rats, that such basal membrane changes manifest themselves relatively early in an increase of basal membrane components in the circulation or in other body fluids.

Another form of pathological basal membrane changes depends upon autoimmune reactions against the body's own basal membrane proteins which, via subsequent reactions, such as inflammation and proteolytic breakdown, can lead to an impairment of the function of basal membranes in various organs, such as the kidneys and lungs. In the case of humans, such diseases include various chronic kidney diseases, multiple sclerosis, diabetes and some rare diseases, such as Goodpasture's syndrome and bullous pemphigoid. It is to be assumed that many of these auto-immune reactions have hitherto not been detected as a result of the lack of suitably sensitive test processes. However, numerous animal experiments have shown that some of the basal membrane components possess autoantigenic properties or that antibodies against these proteins bring about pathological changes.

Basal membrane collagen (Type IV) is a component occurring in all basal membranes and, besides other functions, is, in particular, responsible for the mechanical stability of these structures. An increased synthesis or destruction of basal membranes should, therefore, be connected with an increased appearance of structures of the basal membrane collagen, for example in the circulation. Basal membrane collagen with a molecular weight of about 600,000 consists of various structural domains: a triple helix with a length of about 330 nm, another triple helix which is shorter and has a length of 60 nm (7S domain) and a globular domain NC1. As a result of covalent cross-linking, the greater part of the basal membrane collagen of the tissue is insoluble. These cross-linkings are, after association of the molecules, formed into large, presumably regular meshworks. The association thereby takes place via the 7S domain and the globular domain NC1, four or two molecules thereby being connected with one another. As a result of this arrangement, the globular domain NC1 of the tissue collagen is, in each case, the association of two different molecules.

It is an object of the present invention to make available the human globular basal membrane collagen domain NC1, to provide a generally usable process for the isolation of the globular domain NC1 of basal membrane collagen and to use this material of human origin, after appropriate marking, for the sensitive and quantitative detection of basal membrane collagen in body fluids. At the same time, the present invention is to make possible the investigation of biological fluids or tissues for the presence of autoantibodies or of autoreactive immune cells.

Thus, according to the present invention, there is provided human globular basal membrane collagen domain NC1, which has a molecular weight of about 170,000 Dalton, determinated by equilibrium-ultra centrifugation and light scattering, a hexameric structure with monomeric subunits with a molecular weight of about 28,000 Dalton and a carbohydrate content of about 2%.

The present invention also provides a process for obtaining and purifying globular basal membrane collagen domain NC1, wherein human or animal tissue is subjected to a first limiting treatment with bacterial collagenase, the degradation products obtained are separated from non-collagen proteins by chromatography on a weakly basic anion exchanger, the collagen degradation products are then subjected to a second collagenase digestion at an elevated temperature and the globular domain NC1 is purified by molecular sieve fractionation.

The process according to the present invention for the purification of globular domain NC1 starts directly from the tissues and omits a previous of the basal membranes, which usually involves great losses. A first limiting treatment of the bacterial collagenase, which dissolves out of the material the globular domain and large pieces of the collagen triple helix in intact form, is important. These components can then easily be separated from accompanying non-collagen proteins, for example laminin, for example on a diethylaminoethanol group-modified carbohydrate, such as DEAE-cellulose. The second collagenase digestion, carried out under more severe conditions, then destroys all collagenous, triple-helical structures with the exception of the cross-linked 7S domain and of the globular domain NC1. Both components can be separated from one another and from accompanying collagenous peptides in a single molecular sieve step, for example on agarose, and are then obtained in high purity.

The process can be applied to various tissues, human placenta, kidney or lung preferably being used. The yield of globular domain NC1 thereby amounts, on average, to 20 mg. per kg. of wet tissue. The process can also be applied to animal tissue, for example to bovine aorta or to the EHS sarcoma of mice.

The process according to the present invention preferably starts from a tissue which has been homogenised in a salt-containing buffer solution. Furthermore, it is advantageous for the subsequent purification of NC1 to extract the tissue, before the first collagenase treatment, with guanidine hydrochloride in the presence of protease inhibitors. It has thereby proved to be especially useful to carry out an extraction with an approximately 0.5M potassium chloride solutin and thereafter with an approximately 6M guanidine-containing solution.

These steps remove a considerable part of the accompanying proteins, without it thereby resulting in a dissolving out or destruction of the globular domain NC1.

The first collagenase treatment is preferably carried out at a temperature of from 15° to 25° C. The second, nonlimited collagenase treatment, on the other hand, is preferably carried out at a temperature of from 30° to 45° C.

After the purification, the globular domain NCl is uniform in the ultracentrifuge and has a molecular weight of 170,00. The structure is principally a hexamer, the monomeric subunits having a molecular weight of 28,000. However, the greater part of the monomers is combined via disulphide bridges or other covalent cross-links to give dimeric subunits. This gives rise to a characteristic electrophoresis pattern ( in the presence of sodium dodecyl sulphate) of one to two monomer bands and two usually stronger dimer bands. This hexameric structure is also stable against proteolytic degradation under physiological conditions, for example neutral buffer. A dissociation into the ubunits takes place at an acidic pH or in the presence of 8M urea. This dissociation is substantially reversible. Dialysis against neutral buffer permits the reconstitution to a hexameric globular structure.

The amino acid compositions of the globular domain NCl from human placenta, kidney or lung are very similar (see the following Table). The carbohydrate content of the material is low (2%) and contains not only glucosamine but also galactosamine. The different subunits of the structure can originate not only from the $\alpha 1(IV)$ chain but also from the $\alpha 2(IV)$ chain of the basal membrane collagen, which chains differ in their structure.

This basal membrane structure NCl, which in the following is referred to as antigen, makes possible the determination according to the present invention of basal membrane collagen in blood and other body fluids, with the use of per se known immunological methods of detection. These methods depend upon the competition of a known amount of marked antigen with an unknown amount of the antigen in the sample to be investigated for a common antibody. There can thereby be used not only known variants of the radioimmune test (RIA) but also the enzyme immune test (EIA). Such methods are well known and do not need to be described here in detail. All these processes depend upon the fact that antisera (antibodies) are produced in appropriate experimental animals with the highly purified antigen and with these or also specific isolated antibodies, by appropriate incubation of the reaction partners, the usual antibody-antigen complexing reaction is allowed to take place. Depending upon the amount of non-marked antigen present in the sample of a body fluid to be investigated, only a part of the marked antigen is bound in this complex and can be measured either by isolation of the complex or in the supernatent. Since the amount of the marked antigen bound in the complex is dependent upon the amount of the non-marked antigen, in this way the content of basal membrane collagen or of domain NCl in the body fluid can be determined.

The preparation of the antisera can take placein the usual way by the subcutaneous injection of experimental animas, preferably rabbits, the antigen preferably being administered together with complete Freund's adjuvant. Two injections of 0.1 to 0.2 mg. of the globular domain NCl as antigen have thereby proved to be sufficient. The antiserum formed is then obtained in the usual way and can be used as such. It is also possible to purify the antibodies present in the serum by affinity chromatography methods.

The marking of the antigen can, in principle, be carried out with the methods known for the introduction of the radionuclide iodine 125 into proteins. The marking of the globular domain with Bolton-Hunter reagent (see Biochem. J., 133, 529–539/1973) has thereby proved to be especially advantageous. Marking by the chloramine T method is less successful and produces marked antigens which only bind to an extent of 20 to 50% to the antibodies.

A preferred embodiment of the determination according to the present invention consists in carrying out the separation of the antigen-antibody complex formed with the specific antiserum by the use of a second antibody (antiserum). As second antibody, there is thereby preferred an antiserum against immunoglobulin G of the type of animal used for obtaining the antiserum. The separation of the antigen-antibody complex, thereby converted into insoluble form, from the solution can take place by methods known for this purpose, for example by centrifuging off. After separation of the antigen-antibody complex, the marking, such as radioactivity or enzyme activity, which is bound in the complex is measured. On the basis of a calibration curve which has been produced by means of samples of known antigen content, the amount of antigen contained in the sample to be investigated can then be ascertained.

The immunological determination process according to the present invention permits the measurements of concentrations in the range of 1 ng/ml. It is thus possible to use this process for the ascertainment of basal membrane collagen in body fluids. In the case of normal individuals, the concentration of the antigen is in the range of 5 to 20 ng/ml. but can be significantly increased in the case of diseases with basal membrane changes, such as diabetes and tumours.

Besides the determination of antigen in biological material, the process can also be employed for the detection of antibodies (preferably auto-antibodies) against the antigen. For this purpose, various dilutions of the potential antibody sources, for example serum, are, as already described, incubated with the marked antigen and the antigen-antibody complex is separated off and analysed for the amount of bound antigen. As a comparison thereto, analogous binding experiments are carried out with a normal serum (negative control). The difference in the bindung activity towards this negative control is then evaluated as a measure for the presence of autoantibodies.

The following Examples are given for the purpose of illustrating the present invention:

EXAMPLE 1

Preparation of globular domain NCl from human tissue 1 kg. of placenta, kidney or lung is homogenised in 5 litres 0.5M potassium chloride solution, 0.1 M tris-HCl (pH 7.4) and stirred for 24 Hours at 4° C. The remaining residue is then extracted once with 2 litres and once with 1 litre of 6M guanidine hydrochloride solution at 4° C. All extraction buffers contain p-hydroxymercuribenzoate and phenylmethanesulphonyl fluoride (20 mg./litre of each) as protease inhibitors. The remaining residue is then dialysed against water and lyophilised. About 20 g. of the lyophilised residue are homogenised in 800 ml. 0.2M sodium chloride, 0.002M calcium chloride, 0.05M tris-HCl (pH 7.4) and digested with 8 mg. bacterial collagenase for 24 hours at ambient temperature. This degradation is again repeated and the combined supernatants are, after the addition of 0.005M EDTA, precipitated with 3M sodium chloride. The precipitate is dissolved in 2M urea, 0.05M tris-HCl (pH 8.6) and applied to a column of DEAE-cellulose (2.5×25 cm.) which is equilibrated in the same buffer. The material which is not bound on the column is dialysed against 0.2M ammonium bicarbonate solution (pH 7.9) and, after the addition of 5 to 10 mg. collagenase, again digested for 24 hours at 37° C. and subsequently lyophilised. The final purification then takes place on an agarose A column (1.5 m.) in 1M calcium chloride, 0.05M tris-HCl (pH 7.4). The products thus obtained have the amino acid compositions given in the following Table:

TABLE

Amino acid composition of the globular domain NCl of basal membrane collagens isolated from human placenta, kidney or lung

|  | placenta | kidney | lung |
|---|---|---|---|
| hydroxyproline | 4 | 8 | 5 |
| aspartic acid | 66 | 67 | 66 |
| threonine | 60 | 55 | 56 |
| serine | 102 | 120 | 123 |
| glutamic acid | 91 | 104 | 104 |
| proline | 67 | 61 | 64 |
| glycine | 88 | 113 | 105 |
| alanine | 69 | 73 | 76 |
| cysteine | 41 | 37 | 36 |
| valine | 42 | 33 | 35 |
| methionine | 17 | 22 | 19 |
| isoleucine | 44 | 40 | 43 |
| leucine | 64 | 71 | 70 |
| tyrosine | 32 | 38 | 39 |
| phenylalanine | 37 | 39 | 39 |
| histidine | 29 | 31 | 32 |
| hydroxylysine | 6 | 8 | 8 |
| lysine | 25 | 26 | 27 |
| arginine | 51 | 54 | 53 |
| tryptophane | 65 | n.b. | n.b. |

EXAMPLE 2

Preparation of marked domain NCl (=antigen)

25 μg. of te globular domain NCl obtained according to Example 1 in 0.05 ml. 0.1M sodium borate solution (pH 8.5) are incubated with 1 mCi iodine 125-marked Bolton-Hunter reagent (3-iodo-1-p-hydroxyphenylpropionic acid N-hydroxysuccinimide ester) for 45 minutes at 45° C. The reaction is stopped by the addition of 0.2 ml. 0.2M glycine in 0.1M borate buffer (pH 8.5). Non-bound reagent is then removed by dialysis against buffer or by gel filtration on BioGel P2.

EXAMPLE 3

Carrying out of an immunological determination (radioimmune test)

The concentration of the globular domain NCl in an unknown serum sample is determined in the following inhibition test:

A definite amount of the specific antibody or antiserum obtained by two injections of 0.15 mg. NCl in complete Freund's adjuvant into rabbits is preincubated with the unknown sample for 16 hours at 4° C. and, after the addition of 1 ng. of marked antigen according to Example 2, incubated for a further 8 hours at 4° C. Thereafter, an excess of antibody against rabbit immunoglobulin G is added thereto and, after a further 16 hours at 4° C., the antigen bound in the immune complex is separated off by centrifugation. The inhibition activity of the unknown sample is compared with the activity of a standard concentration of non-marked antigen.

We claim:

1. A process for isolating and purifying globular domain NCl from basal membrane collagen comprising extracting globular domain NCl containing tissue with guanidine hydrochloride to obtain a globular NCl containing extract treating said extract with bacterial collagenase to degrade collagen fragments in said extract separating the degradation products obtained from non-collagenous proteins by chromatography on a weakly basic anion exchanger, treating the collagen degradation products a second time with collagenase at an elevated temperature and purifying the globular domain NCl by molecular sieve fractionation.

2. The process of claim 1, wherein said tissue is homogenised in a salt-containing buffer solution before subjecting to the first treatment.

3. The process of claim 1, wherein said tissue is derived from tissue, human placenta tissue, human kidney tissue, human lung tissue bovine aorta tissue or EHS sarcoma tissue.

4. The process of claim 1, wherein the first collagenase treatment is carried out at a temperature of from 15° to 25° C.

5. The process of claim 1, wherein the second collagenase digestion is carried out at a temperature of from 30° to 45° C.

6. The process of claim 1, wherein said anion exchanger is a diethylaminoethanol group-modified carbohydrate.

7. The process of claim 1, wherein the first collagenase treatment is carried out at a temperature of from 15° to 25° C., the second collagenase treatment is carried out at a temperature of from 30° to 45° C. and said anion exchanger is a diethylaminoethanol group-modified carbohydrate.

* * * * *

UNITED STATES PATENT AND TRADEMARK OFFICE
CERTIFICATE OF CORRECTION

PATENT NO. : 4,798,800
DATED : January 17, 1989
INVENTOR(S) : Rupert Timpl, etal.

It is certified that error appears in the above-identified patent and that said Letters Patent is hereby corrected as shown below:

Column 2, line 33: after "previous" insert -- purification --.

Column 3, line 8: change "170,00" to -- 170,000 --;
line 18: change "ubunits" to -- subunits --.

Abstract, line 2: after "human" insert -- globular domain NC1 of basal membrane collagen --;
line 18: after "this" insert -- globular domain NC1 --.

Signed and Sealed this

Third Day of October, 1989

Attest:

DONALD J. QUIGG

Attesting Officer

Commissioner of Patents and Trademarks